US006892084B2

United States Patent
Eppich et al.

(10) Patent No.: US 6,892,084 B2
(45) Date of Patent: May 10, 2005

(54) METHOD FOR ANALYZING SUBSTANCE MIXTURES

(75) Inventors: Bernd Eppich, Berlin (DE); Gerhard Müller, Berlin (DE)

(73) Assignee: Becton Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 10/258,003

(22) PCT Filed: Apr. 6, 2001

(86) PCT No.: PCT/EP01/03934

§ 371 (c)(1),
(2), (4) Date: Apr. 15, 2003

(87) PCT Pub. No.: WO01/79815

PCT Pub. Date: Oct. 25, 2001

(65) Prior Publication Data

US 2003/0151009 A1 Aug. 14, 2003

(30) Foreign Application Priority Data

Apr. 17, 2000 (DE) .......................... 100 18 941
Apr. 17, 2000 (DE) .......................... 100 18 940

(51) Int. Cl.$^7$ .............................................. A61B 5/00
(52) U.S. Cl. ........................................ 600/316; 600/310
(58) Field of Search ................................. 600/316, 365, 600/310

(56) References Cited

U.S. PATENT DOCUMENTS

| 5,221,959 | A |   | 6/1993  | Ohyama et al. |
|-----------|---|---|---------|---------------|
| 5,461,475 | A | * | 10/1995 | Lerner et al. ............... 356/300 |
| 5,631,469 | A |   | 5/1997  | Carrieri et al. |
| 5,748,308 | A |   | 5/1998  | Lindberg et al. |

FOREIGN PATENT DOCUMENTS

WO     WO 99/09395     2/1999

* cited by examiner

*Primary Examiner*—Eric F. Winakur
*Assistant Examiner*—Matthew Kremer
(74) *Attorney, Agent, or Firm*—Hoffmann & Baron, LLP

(57) ABSTRACT

Method for filter selection of binary configured for determining smallest concentration changes in substance mixtures is provided wherein one or a plurality of low-concentration lead components can be reliably detected in the presence of higher-concentration matrix or background components using the selected broad-band binary filters. The spectral power transmitted or reflected by the substance mixture is detected by a plurality of photosensitive detectors which are spectrally broad-banded and provided with binary filters, the detector signals being used for exact determination of the substance concentrations.

15 Claims, 13 Drawing Sheets

```
Read in matrix E                                        //Reading-in of input data Nz = lines (E)                                          //Number of lines of matrix E
Ns = columns (E)                                        //Number of columns of matrix E R = matrix (Ns,Nz)                                      //Generated matrix with Ns lines and Nz columns //Initialization of matrix
for iz = 0..Nz-1                                        //Iteration across all columns
  for is = 0..Ns-1                                      //Iteration across all lines
    if (iz = is)
      R_{iz,is} = 1                                     //Setting of an element to One in each line
    otherwise
      R_{iz,is} = 0                                     //Setting of all other elements to Zero Repeat
  for is = 0..Ns-1                                      //Iteration across all lines of matrix R
    V = vector (Nz)                                     //Generation of vector of length Nz
    calculate V from R, E and iz acc. to equation (18)  //Calculation of the elements of the vector
    for iz = 0..Nz-1                                    //Iteration across all columns
      if ((V)_{iz} > 0)                                 //Resetting of elements in the isth line of matrix R
        R_{is,iz} = 1
      otherwise
        R_{is,iz} = 0
until matrix R does not change any more
```

Fig. 6

METHOD FOR ANALYZING SUBSTANCE MIXTURES

CROSS-REFERENCE TO RELATED APPLICATIONS

This application is a National Phase filing under 35 U.S.C. §371 of PCT/EP01/03934, filed Apr. 6, 2001, which claims priority to DE 100 18 941.5, filed Apr. 17, 2000 and to DE 100 18 940.7, filed Apr. 17, 2002, all of which are incorporated herein by reference.

FIELD OF THE INVENTION

The invention relates to a method which permits changes in substance mixtures to be detected and quantified on the basis of the change of their spectral signature.

BACKGROUND OF RELATED TECHNOLOGY

It is known that by application of methods of emission and reflectance spectral analysis and evaluation of the state-specific spectral lines as compared with reference standards an analysis of substance mixtures can be carried out. This applies to both the emission spectroscopy by thermal and/or electrical excitation and laser-induced or generally light-induced plasma excitation. Further this applies to the absorption, reflectance and transmission spectroscopy using suitable transmitters in the overall range of electromagnetic radiation. Drawbacks of such spectroanalytical and photometric methods are the fact that in the range of lowest concentration and conformation changes spectral signatures on a very high background are to be detected and that simultaneously the spectral response of the background signal is subjected to strong fluctuations due to ambient and environmental influences. This is for example the case in complex substance mixtures with time-variable or state-variable concentration ratios where frequently the problem arises that one or more lead components of lower concentration are to be detected in the presence of higher-concentration matrix or background components. When the change to be detected in a lead component is equal to or smaller than the statistical or systematical fluctuation of the multi-component mixture or substantial background signals, the application of spectrally high-resolution methods is problematic since in the available detectors, where the spectral bandwidth is narrowed, the interference-signal-to-useful-signal ratio increases. So far this problem has led to failure of spectroanalytical and photometrical methods for detecting small relative concentration changes.

SUMMARY OF THE INVENTION

It is therefore intended to suggest a method where the known drawbacks of spectrally high-resolution one-channel or multi-channel systems are eliminated, wherein simultaneously the sensitivity is increased and the selectivity is maintained.

It is known that by applying methods of the Fourier transform-spectroscopy, possibly in conjunction with so-called chemometrical evaluation methods, or by applying the multi-component cross-analysis for multi-channel spectra, the sensitivity of detection of small changes in substance and concentration even at a higher interference level can be substantially increased as compared with a conventional spectro-absorption photometer (see for example patent U.S. Pat. No. 5,857,462). However these methods of multiplex spectroscopy normally fail, too, when the signal magnitude of the interference background and the associated statistical or systematical fluctuations of the spectral intensity control the dynamics of the given detector. Other solution-finding approaches, such as the use of so-called Girard gratings and the Hadamard transform, do in these cases not produce any satisfactory results.

Recently particular attention has been paid to the broad-band detection of spectral signals (see for example L. A. Sodickson "Improvements in Multivariate Anaylsis via Kromoscopic Measurement" in Molecular Spectroscopy, 12(7) 1997, pages 13–21). Due to omission of the spectral narrowing during detection and the resultant higher light level per detector the signal-to-noise ratio is improved. It is known that the detection accuracy of concentration changes depends to a high degree on the spectral filters and the spectral sensitivity of the detectors. However no method is known by means of which optimum filtering patterns can be analyzed. Rather, filtering patterns are subjectively selected or parametrized filtering patterns are matched by sophisticated optimization algorithms. In this connection smooth, i. e. gradually ascending and descending, filtering patterns are selected as is shown by way of example in FIG. 9.

Surprisingly it has turned out that due to the modification of the spectroanalytical detection approach according to the invention, i. e. in that instead of a continuous spectrum one or a plurality of spectrally limited bandpass response signals are detected and algorithmically combined in a suitable manner, the invention-essential claim regarding detection of smallest concentration changes in heterogeneous gaseous, liquid or solid substance mixtures is complied with. The solution-finding approach according to the invention proceeds from the assumption that in the case of detection of a plurality of possibly overlapping spectral windows an algorithm can always be found by means of which the percentage associated with the individual spectral windows of the absorption or emission characteristic determined by concentration changes can be detected and analyzed by suitable evaluation.

BRIEF DESCRIPTION OF THE DRAWINGS

FIG. 6 is a schematic of the method of the present invention for determining the filter matrix.

DETAILED DESCRIPTION OF THE INVENTION

Surprisingly it has turned out that in the event of an approximately linear correlation between changes in the substance concentrations and changes in the spectral power of the emission, reflectance or transmission signal the matched optimum filtering functions must always be binary, i. e. the filtering functions of each matched and optimized detector in the respective bandpass spectral range must always be equal to 1 or 0.

Figure 1:
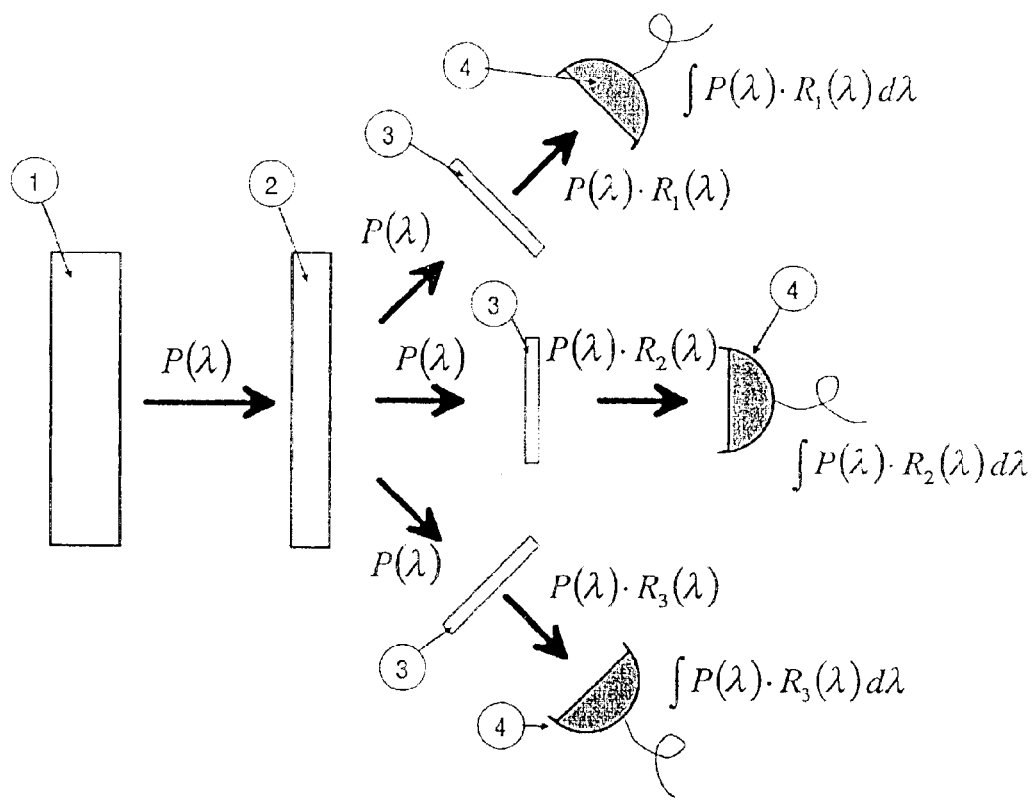
FIG. 1 is a schematic of the measuring setup of the present invention for determining changes in substance concentrations.

According to FIG. 1 $P(\vec{C},\lambda)$ be the spectral power delivered by the substance mixture due to emission, reflectance or transmission. In the case of otherwise given conditions (radiated power, geometry) it be only dependent on the concentrations $C_1, C_2 \ldots C_N$ of the N substances which can be combined in the so-called concentration vector $$\vec{C} = (C_1\ C_2 \ldots C_N)^T \tag{1}$$

and on the wavelength $\lambda$. If the spectral power is discreted with regard to the wavelength, a vector is obtained which represents the spectral power according to the equation:

$$\vec{P}(\vec{C}) = (P_1(\vec{C})\ P_2(\vec{C}) \ldots P_L(\vec{C}))^T \tag{2}$$

where $$P_l(\vec{C}) = P(\vec{C},\lambda_l). \tag{3}$$

At least for sufficiently small changes in the concentrations the dependence of the spectral power on the concentrations can be represented in good approximation by a Taylor development:

$$\vec{P}(\vec{C}_0+\delta\vec{C}) = \vec{P}(\vec{C}_0) + \nabla_{\vec{C}}\vec{P}(\vec{C})|_{\vec{C}=\vec{C}_0} \cdot \delta\vec{C}. \tag{4}$$

Thus the change in the spectral power as a function of the change in the concentrations can be represented by a simple matrix equation, namely:

$$\delta\vec{P} = E \cdot \delta\vec{C} \tag{5}$$

where $$\delta\vec{P} = \vec{P}(\vec{C}+\delta\vec{C}) - \vec{P}(\vec{C}) \tag{6}$$

and $$E = \nabla_{\vec{C}}\vec{P}(\vec{C})|_{\vec{C}=\vec{C}_0}. \tag{7}$$

If the spectral power $\vec{P}$ is detected by a photosensitive detector having a spectral response of $0 \leq R(\lambda) \leq 1$, said spectral power produces a signal according to the equation:

$$S(\vec{C}) = \vec{R} \cdot \vec{P}(\vec{C}) \tag{8}$$

wherein the spectral response $R(\lambda)$ is again represented as a vector after discreting with regard to the wavelength, namely:

$$\vec{R} = (R_1\ R_2 \ldots R_L),\ R_l = R(\lambda_l). \tag{9}$$

If a number of $D > 1$ detectors is considered, their signals can also be combined into a common signal vector $\vec{S}$ whose dth element corresponds to the signal $S_d$ of the dth detector. Then the following functional correlation between the signal vector and the concentration vector is obtained:

$$\vec{S} = R \cdot E \cdot \vec{C} \tag{10}$$

having a response matrix of $$R = \begin{pmatrix} \vec{R}_1^T \\ \vec{R}_2^T \\ \vdots \\ \vec{R}_D^T \end{pmatrix} = \begin{pmatrix} R_{1,1} & R_{1,2} & \cdots & R_{1,L} \\ R_{2,1} & R_{2,2} & \cdots & R_{2,L} \\ \vdots & \vdots & \ddots & \vdots \\ R_{D,1} & R_{D,2} & \cdots & R_{D,L} \end{pmatrix} \tag{11}$$

whose dth line is determined by the spectral response of the dth detector and to whose element $R_{dl}$ corresponds the response of the dth detector at wavelength $\lambda_l$. Changes in the concentration vector now effect changes in the signal vector according to the equation:

$$\delta\vec{S} = M \cdot \delta\vec{C}, \tag{12}$$

which can mathematically be considered as a mapping imparted by the matrix:

$$M = R \cdot E \tag{13}$$

$$= \begin{pmatrix} \vec{R}_1^T \\ \vec{R}_2^T \\ \vdots \\ \vec{R}_D^T \end{pmatrix} \cdot (\vec{E}_1\ \vec{E}_2\ \cdots\ \vec{E}_N)$$

$$= \begin{pmatrix} \vec{R}_1^T \vec{E}_1 & \vec{R}_1^T \vec{E}_2 & \cdots & \vec{R}_1^T \vec{E}_N \\ \vec{R}_2^T \vec{E}_1 & \vec{R}_2^T \vec{E}_2 & \cdots & \vec{R}_2^T \vec{E}_N \\ \vdots & \vdots & \ddots & \vdots \\ \vec{R}_D^T \vec{E}_1 & \vec{R}_D^T \vec{E}_2 & \cdots & \vec{R}_D^T \vec{E}_N \end{pmatrix}$$

of the N-dimensional concentration vector changes into D-dimensional signal vector changes. According to the invention the causal concentration changes are to be determined from the signal vector changes by suitable mathematical operations. The accuracy attainable essentially depends on the response matrix R, i. e. the spectral response of the D detectors. The variation of the concentration vector can be described by the overlined N-dimensional volume in the concentration room and the resultant variation of the signal vector by an N-dimensional volume in the D-dimensional signal vector room. The maximization of the ratio of the overlined signal room volume to the overlined concentration room volume is thus the optimization criterion. Mathematically this is equivalent to the maximization of the value of the Gram determinant of the matrix $M = R \cdot E$ imparting the mapping, namely:

$$|\det(M^T \cdot M)| \to \max. \tag{14}$$

If the number of detectors is advantageously selected such that is equals the number of the varying concentrations, $D = N$, the matrix M becomes squared and the following is obtained:

$$\det(M^T \cdot M) = \det(M)^2, \tag{15}$$

such that the maximization of the Gram determinant is attributable to the maximization (or minimization) of the determinant of the matrix M. This leads to the binarity of the optimum response matrix R, i. e. to the fact that all relevant elements of this matrix and thus all elements which influence the optimization criterion must be either 1 or 0. Advantageously possible non-relevant elements of R are also set to Zero.

For proving the binarity it be assumed that the optimum response matrix $R_{opt}$ has already been found. Since this optimum response matrix maximizes the determinant of the matrix $M=R \cdot E$ as per definition, the partial derivations according to all elements of the matrix R must disappear. The determinant of the matrix M can be expressed as follows by the column vector of the matrix R and the line vectors of the matrix E:

$$\det(M) = \sum_{\pi} \vec{R}_1^T \vec{E}_{\pi(1)} \cdot \vec{R}_2^T \vec{E}_{\pi(2)} \ldots \vec{R}_N^T \vec{E}_{\pi(N)}, \quad (16)$$

where the sum must be determined for all permutations $\pi$ of the FIGS. 1 to N.

Considering the dependence of the determinant on the spectral response of any detector d, the following is obtained:

$$\det(M) = \vec{R}_d^T \cdot \vec{V}_d, \quad (17)$$

where the vector $V_d$ is calculated from the system matrix E and the spectral sensitivities of all other detectors according to the equation:

$$\vec{V}_d = \sum_{\pi} \vec{R}_1^T \vec{E}_{\pi(1)} \cdot \vec{R}_2^T \vec{E}_{\pi(2)} \ldots \quad (18)$$

$$\vec{R}_{d-1}^T \vec{E}_{\pi(d-1)} \cdot \vec{R}_{d+1}^T \vec{E}_{\pi(d+1)} \ldots \vec{R}_N^T \vec{E}_{\pi(N)}$$

Then the partial derivation of equation (17) with regard to any nth element of the response vector is:

$$\frac{\partial}{\partial R_{d,n}} \det(M) = \frac{\partial}{\partial R_{d,n}} \vec{R}_d^T \cdot \vec{V}_d = \left(\vec{V}_d\right)_n. \quad (19)$$

When the right-hand side of equation (19) disappears, element $R_{d,n}$ is irrelevant to the determinant. Otherwise equation (19) contradicts the proposition such that the matrix R cannot be the optimum response matrix. Thus all relevant elements of the matrix must lie at the margin of their range of values, i. e. must equal Zero or One.

In view of this surprising result an iterative process for numerical determination of the optimum response matrix is derived from a known system matrix E. The process starts with any response matrix R not exclusively made up of Zeros. From this matrix and the matrix E the vector $V_1$ is calculated according to equation (18). According to the values of this vector the values of the first line of matrix R are now newly set such that the ith value of the line is set to One when the ith component of vector $V_1$ is larger than Zero, or is otherwise set to Zero, i. e.

$$R_{d,i} = \begin{cases} 1 & \text{if } \left(\vec{V}_d\right)_i > 1 \\ 0 & \text{otherwise} \end{cases}. \quad (20)$$

Using the new values of matrix R the vector $V_2$ is determined next and accordingly the second line of matrix R is newly set, and so on, up to the last line of matrix R. Starting with the first line this process is repeated until the values of matrix R do not change any more. It turned out that the thus produced response matrix R is an optimum matrix in that there is no other matrix which maps a variation of the concentration vector into a larger variation of the signal vector.

The measurement of substance concentrations is now carried out by configuration of detectors which are provided with binary filters according to the determined response matrix. From the signal vectors measured with the aid of this detector arrangement, which are made up of the signals from the individual detectors, the required concentrations can be determined by resolving equation (10), namely:

$$\delta \vec{C} = (M^T \cdot M)^{-1} \cdot M^T \cdot \delta \vec{S}_w, \ M = R \cdot E \quad (21)$$

Surprisingly it further turned out that with the aid of the same approach not only concentration changes but also changes in the ambient parameters, e. g. temperature or pressure, can be taken into consideration if the effect of these changes can be linearized in sufficient approximation. This be represented by way of example on the basis of the dependence of the spectral power P on the temperature T, i. e.

$$P = P(\vec{C}, T, \lambda). \quad (23)$$

The linear approximation is obtained by extending equation (4) according to the following equation:

$$P(\vec{C}_0 + \delta \vec{C}, T_0 + \delta T) = P(\vec{C}_0, T_0) + \quad (24)$$

$$\nabla_{\vec{C}} P(\vec{C}, T)\bigg|_{\substack{\vec{C}=\vec{C}_0 \\ T=T_0}} \cdot \delta \vec{C} +$$

$$\frac{\partial}{\partial T} P(\vec{C}, T)\bigg|_{\substack{\vec{C}=\vec{C}_0 \\ T=T_0}} \cdot \delta T.$$

Thus the change in the spectral power as a function of the change in concentrations and temperature can, in turn, be represented by a simple matrix equation, namely:

$$\delta \vec{P} = E' \cdot \delta \vec{C}' \quad (25)$$

with the extended concentration vector:

$$\vec{C}' = \begin{pmatrix} \vec{C} \\ T \end{pmatrix} \quad (26)$$

and the extended system matrix:

$$E'_{i,j} = \begin{cases} \left.\dfrac{\partial}{\partial C_j}P(\vec{C}, T, \lambda_i)\right|_{\substack{\vec{C}=\vec{C}_0 \\ T=T_0}} & \text{if } j \leq J \\ \left.\dfrac{\partial}{\partial T}P(\vec{C}, T, \lambda_i)\right|_{\substack{\vec{C}=\vec{C}_0 \\ T=T_0}} & \text{if } j = J+1 \end{cases} \quad (27)$$

The effect of variable ambient parameters can thus be considered a concentration change of additional virtual substances. Proceeding from the extended system matrix the further steps for determining the optimum response matrix remain the same.

So far it has been assumed that the number of varying substances and ambient parameters as well as the functional correlation between them and the spectral power to be detected are known. In general practice this will frequently not be the case.

Surprisingly it turned however out that the optimum filtering can also be determined on the basis of calibration measurements taken on the system as is known from the chemometry. The power delivered by the substance mixture by emission, transmission or reflectance must be repeatedly measured in the overall wavelength range of interest under varying test conditions. The crucial point is that all variations of substance concentrations and ambient parameters to be expected during subsequent measurements which, according to the invention, are taken for determining the concentration of one or a plurality of substances reappear in the calibration data set. These variations need not be deliberately produced but may also be caused by random or statistical fluctuations. The concentration of the substances to be determined later, according to the invention, must however be known, either by deliberately influencing the system or by determining it by means of a reliable reference measuring method. For evaluation of such calibration measurements in accordance with the chemometry different methods, e. g. the so-called principal component regression or the partially least squares regression, are known. Although such methods have originally aimed at developing a model for determining substance concentrations from measured spectra it surprisingly turned out that these methods can also be applied for the purpose of determining the optimum response matrix. One example in this regard is the known principal components regression. For defining the calibration data a sufficient number K of substance mixtures must be produced. For each substance mixture the emission or reflectance spectrum is determined by means of a spectrum-resolving detector. Then the spectral measuring data are column-wise combined into a matrix B. The matrix is line-wise centered, i. e.

$$\tilde{B}_{i,j} = B_{i,j} - \frac{1}{K}\sum_j B_{i,j}. \quad (28)$$

From the thus determined matrix B the covariance matrix H is determined according to the following equation:

$$H = B \cdot B^T \quad (29)$$

from which, in turn, the eigenvalues and eigenvectors are determined. The K eigenvectors with the maximum associated eigenvalues are column-wise combined into a matrix X, with the number K corresponding to the number of variables of the system, if said number is known, or otherwise being determined according to one of the methods known in the field of chemometry. The columns of the matrix X represent the known prinicpal components of the system. The matrix X is also termed loading matrix and replaces the unknown system matrix E in the calculation described above of the response matrix R. Although the loading matrix X is generally not identical with the actual system matrix E it supplies the correct optimum response matrix.

Based on these surprising findings regarding the spectroanalytical procedure, in a preferred embodiment a set of N optimum filters is used according to the described algorithm, in dependence on the apparatus, in a time-sequential or time-parallel manner to analyze the smallest possible concentration differences. In the simplest case this can be realized by wave-selective beam splitters or reflection filters and a set of N spectrally matched detectors. According to the invention detection of the useful signal via a fibre-optical bundle is also possible wherein individual or groups of fibres are fed via a respective matched spectral filter to a detector configured according to the invention.

In the event of small time fluctuation of the measuring signal time-sequential detection of the individual signal intensities filtered in a spectrally optimum manner is possible according to the invention.

According to one aspect of the inventive concept the individual elements of the determined filter matrix R are checked for their relevance to maximization of the signal variations by partially differentiating the determinant of the matrix product of filter matrix and system matrix E according to the respective element. The value of this partial differentiation is a comparative quantity for the relevance of the corresponding matrix element. With regard to a simpler technical realization of the filters the filters may differ from the actually calculated filter matrix values according to the relative relevance of the corresponding matrix elements.

Surprisingly it further turned out that such a binary bandpass-optimized filtering method is not only of use in the range of the ultraviolet, visible or infrared light for improved spectroanalytical determination of concentration or conformation changes but that this method generally applies to the overall spectral range of electromagnetic radiation so that it is also possible to apply the same basic principle in the range of gamma radiation such as X-radiation of the visible light, the infrared, the far-infrared up to high-frequency radiation. Such spectrally matched optimum filtering functions according to the algorithmic methods described here are also possible according to the invention.

Figure 8:
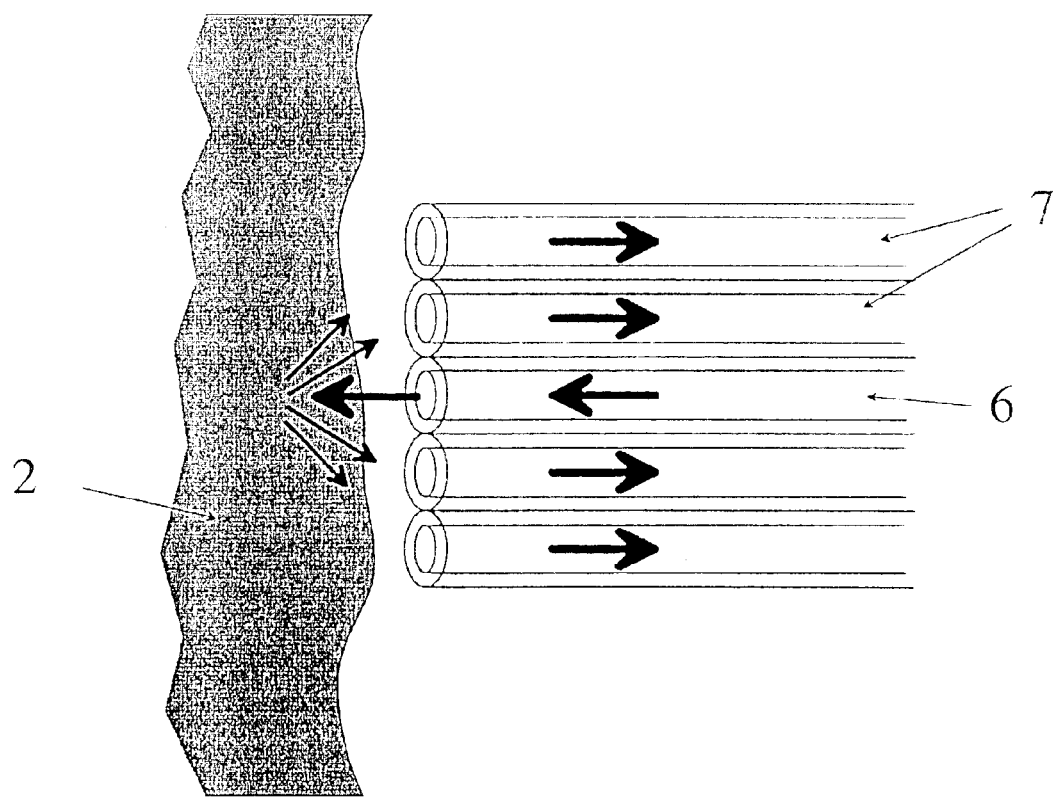
FIG. 8 is a depiction of glass fibers of the present invention for delivering and receiving radiation.
Figure 11:
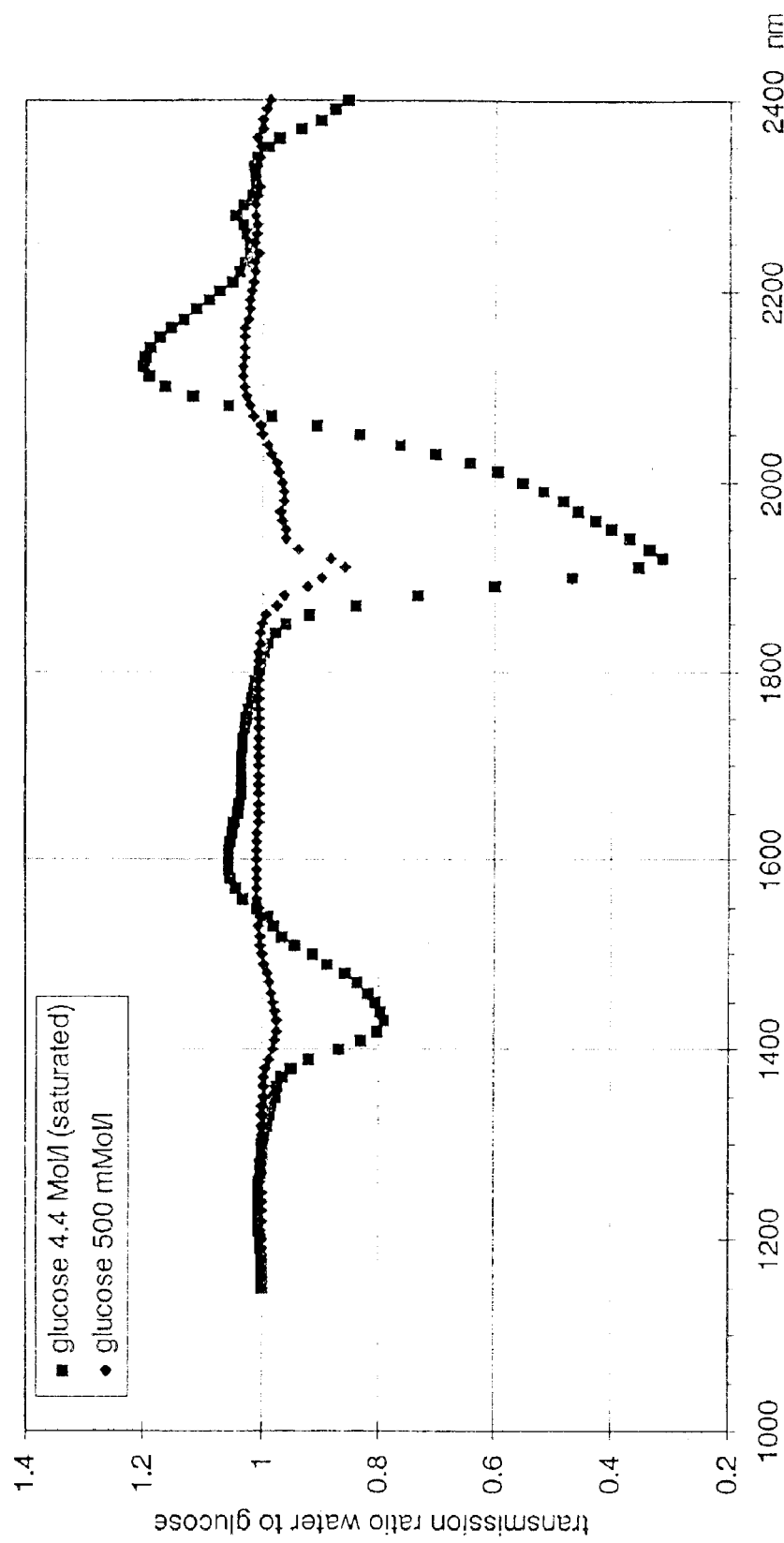
FIG. 11 depicts absorption maxima and minima of glucose relative to water.
Figure 12:
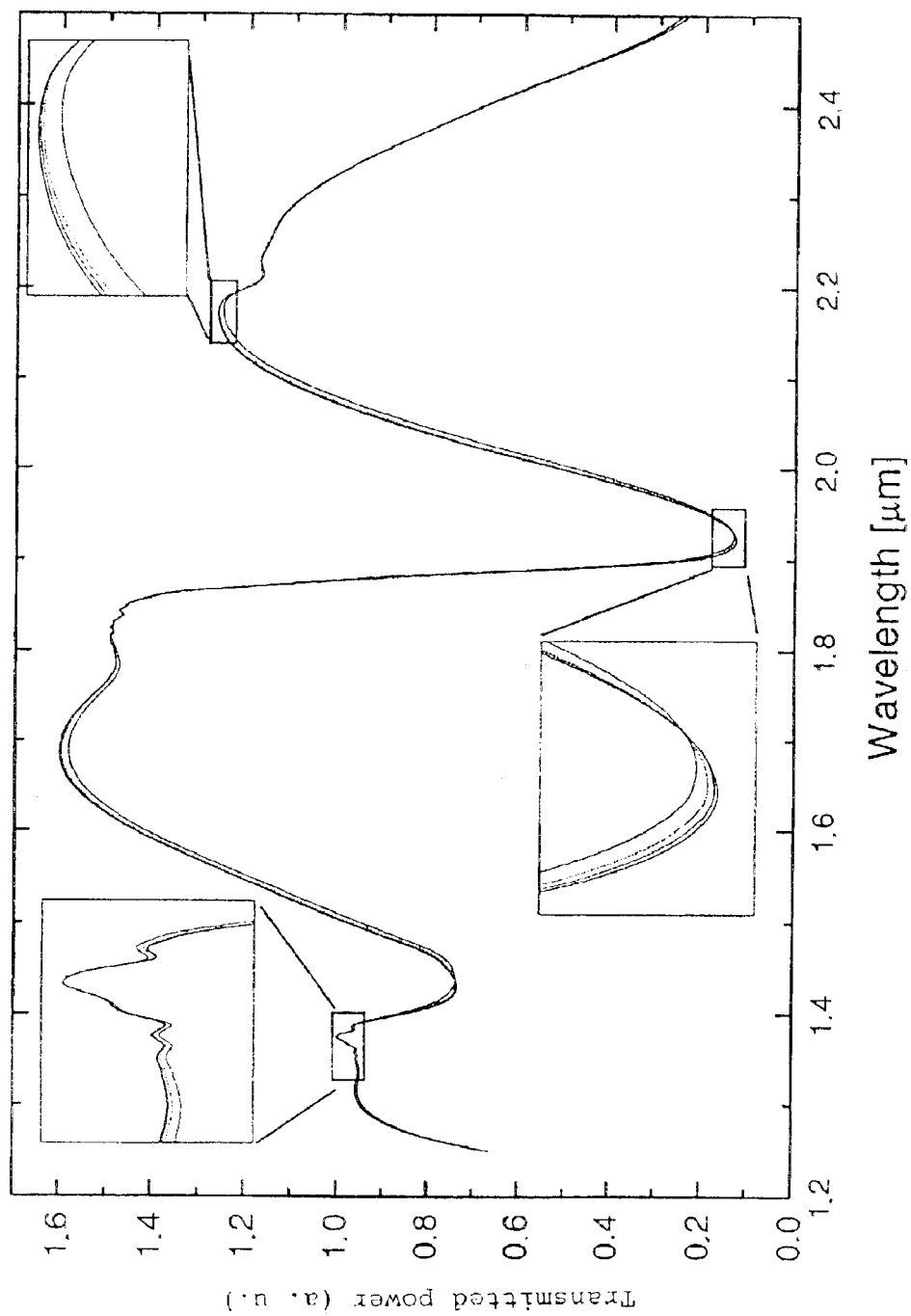
FIG. 12 depicts temperature dependence of the transmission of water from 1.2 $\mu$m to 2.5 $\mu$m.

In a preferred embodiment the metabolism-induced change in the blood glucose of a living organism is to be determined, by way of example, in a transcutaneous manner. For this purpose one bandpass filter each is used for the temperature-independent vibrational band of the water at 1380 nm as shown in FIG. 12 and one bandpass filter each is used for the known absorption maxima of the glucose at 1400 nm and the known absorption minimum at 1900 nm as shown in FIG. 11. In this connection the signal of the temperature-independent water band serves as an internal standard and the signal differences between the off-band and the on-band glucose filters serve for detection of the substance-specific variation as compared with the dynamically changing background signal. The spectral width of the bandpass filter is selected such that the resulting intensity signal possibly lies in the linear dynamic range of the detector due to subsequent optical wedge reduction and that the statistical noise caused by wavelength fluctuation in the light source and the quantal noise and other interferential noise respectively is smaller as compared with the detected signal level than the differential measured variable to be expected. In the preferred embodiment the concentration of blood glucose is modulated in a time-variable manner by the pulsation, whereas the concentration of glucose in the interstitial liquid and inside the cells is a comparatively stable background quantity. In concrete terms this means that the portion of blood glucose is detected either by a stop-flow method, i. e. stopping the blood flow by compression and subsequent decompression and measuring the increasing value, or by a lock-in technique at the low frequencies of the pulsation, or by cross-correlation techniques. According to the invention a thermal light emitter is used as light source in the spectral range of interest between 600 nm and 2.5 μm, however use of sufficiently broad-band laser radiation sources or the combination of a plurality of individual laser radiation sources emitting in a broad band is also possible according to the invention. The supply of radiation to the place of examination is effected by a suitable optical device. According to the invention supply via glass fibre cable is also possible as shown in FIG. 8.

Detection of the transmitted or reflected radiation is effected by means of a suitable optical device, e. g. a collective lens. Then the radiation is split up by one or a plurality of beam splitters and fed to the individual photosensitive detectors as shown in the figures. However, according to the invention reception of the transmitted or reflected radiation by a glass fibre bundle is also possible wherein each individual fibre or a plurality of fibres of the bundle are fed to one of the detectors such that employment of a beam splitter is not necessary as shown in FIG. 8. In a preferred embodiment a single fibre bundle is used for both illumination and detection during reflectance measurements such that one or a plurality of fibres of the bundle feed the radiation from the light source to the place of examination and the remaining fibres of the bundle feed the reflected radiation to the individual detectors.

Figure 13:
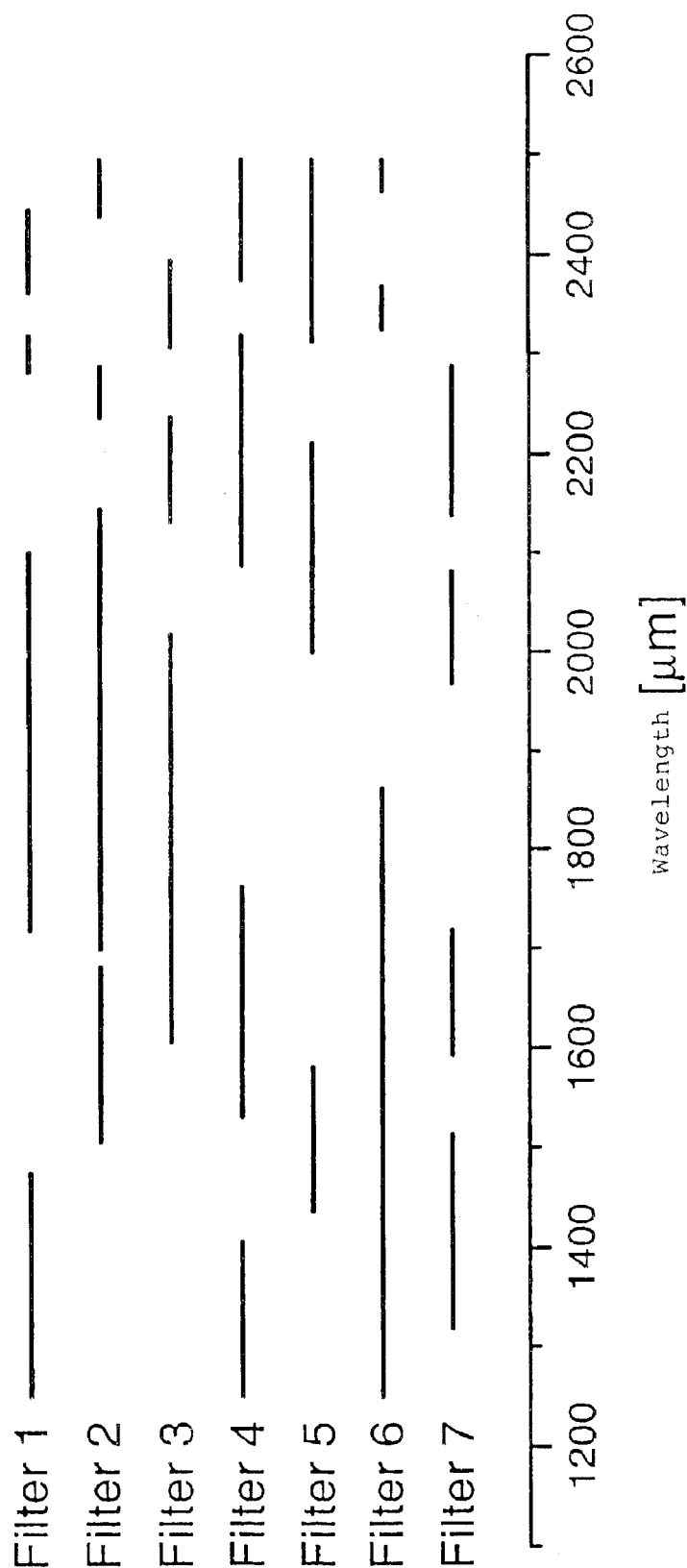
FIG. 13 depicts binary filtering patterns for the transcutaneous determination of blood glucose concentrations.

According to another aspect of the inventive concept experiments have shown that for the transcutaneous determination of blood glucose, taking into consideration temperature dependencies and scattering, use of a number of five to eight detectors each having three to four different transmitting spectral sub-ranges is optimum. In another preferred embodiment seven detectors are employed. The filtering patterns of the individual detectors are again binary with transmitting spectral subranges as shown in FIG. 13. In FIG. 13 horizontal lines mark the spectral subranges for each of the seven filters where the transmission of the respective filter essentially equals One. In all other spectral subranges the transmission of the respective filter essentially equals Zero. The filtering patterns shown result in changes in the glucose concentration causing maximum changes in the detector signals.

FIG. 1 shows the measuring setup according to the invention for determining smallest changes in substance concentrations. The spectal power P(λ) leaving the substance mixture 1 is split up into N partial beams by a beam splitter 2. After transmission of the respective spectral filters 3 the remaining radiant power is determined by means of the broad-band detectors 4. The spectral filters 3 are of essentially binary configuration, i. e. they show, depending on the wavelength, only transmissions essentially equalling Zero or One. Determination of the transmitting spectral subranges is effected according to the aforementioned algorithm. Thus changes in the substance mixture cause maximum changes of the signal vector made up of the signals from the individual detectors.

Figure 2:
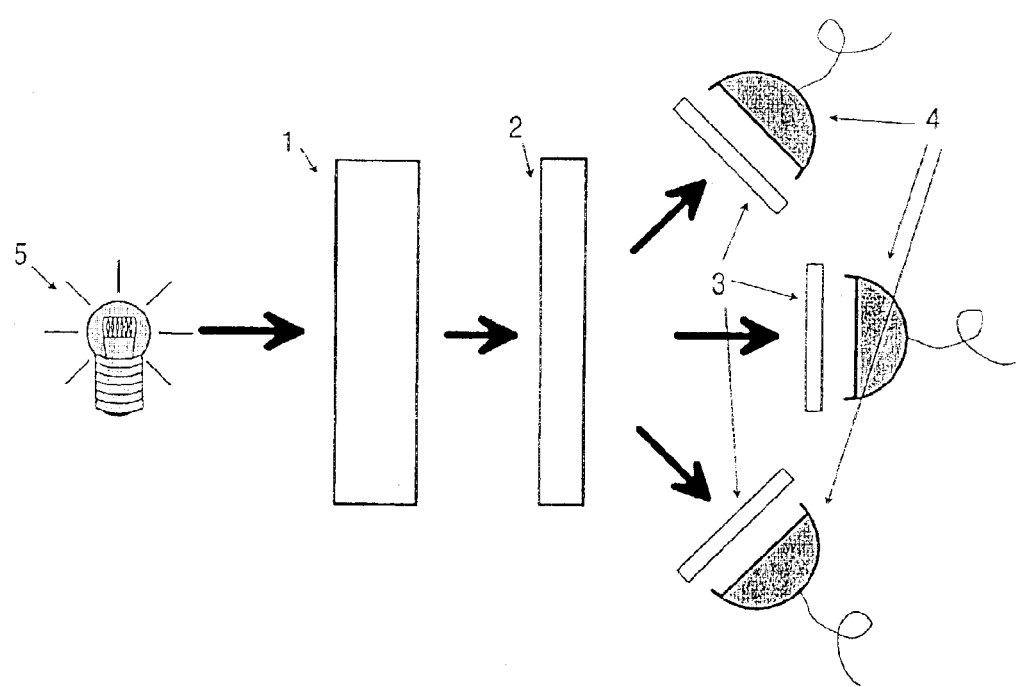
FIG. 2 is a schematic of the measuring setup of the present invention under transmission conditions.

FIG. 2 shows a measuring setup according to the invention for determining smallest changes in substance mixtures under transmission conditions. The light emerging from a radiation source 5 changes its spectral power due to transmission through the substance mixture 1. The spectrum of the transmitted radiation depends on the concentrations of the substances and the ambient parameters. A beam splitter 2 splits the beam into N partial beams which are detected by detectors 4 after transmission of the respective different broad-band binary detector filter 3. Use of binary filters maximizes the photon yield whereby an optimum signal-to-noise ratio is attained. The spectral bandwidth of the passband of the respective filters is selected such that changes in the substance concentrations cause maximum changes in the detector signals.

Figure 3:
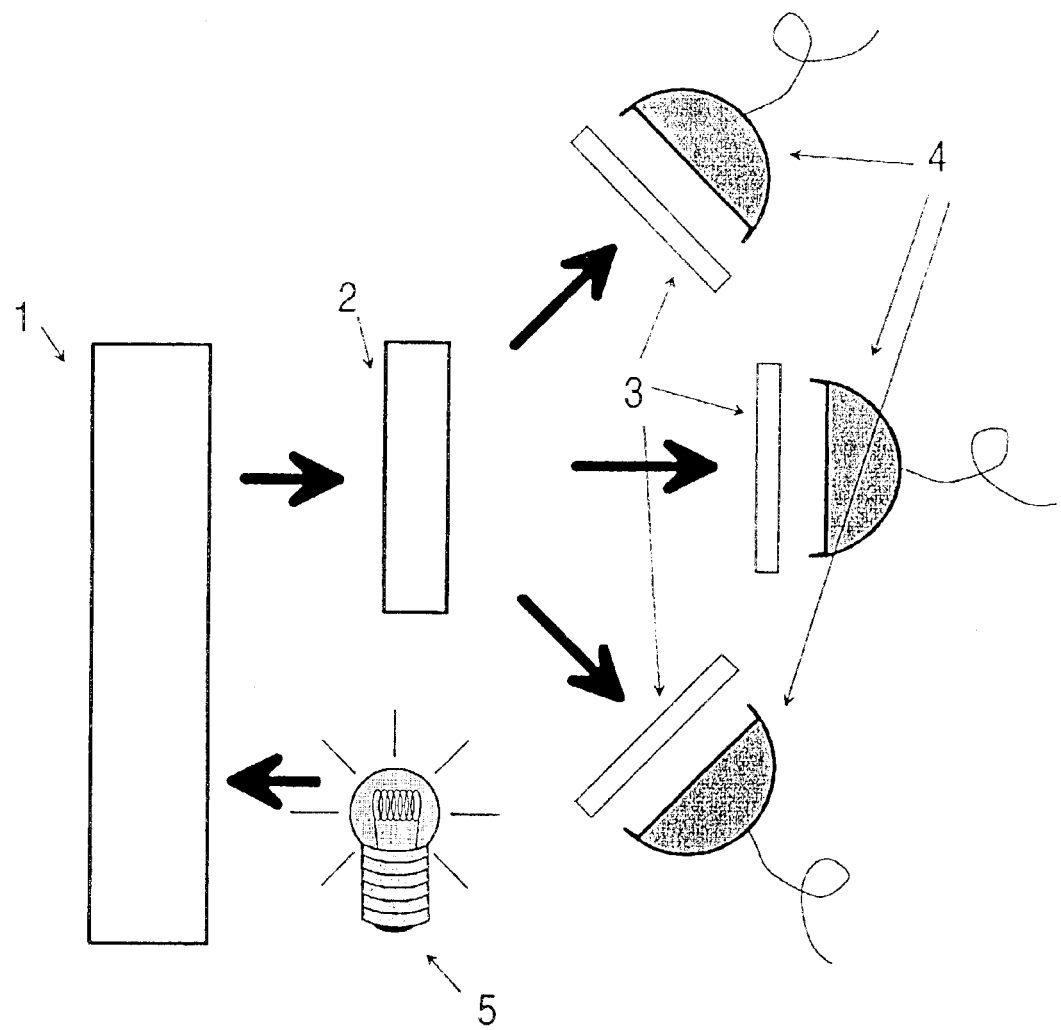
FIG. 3 is a schematic of the measuring setup of the present invention under reflectance conditions.

FIG. 3 shows a measuring setup according to the invention for determining smallest changes in scattering substance mixtures under reflectance conditions. The spectral power of the light emerging from a radiation source 5 is changed by scattering and reflectance in the substance mixture 1. A beam splitter 2 splits the beam into N partial beams which are detected by detectors 4 after transmission of the respective detector filter 3.

Figure 4:
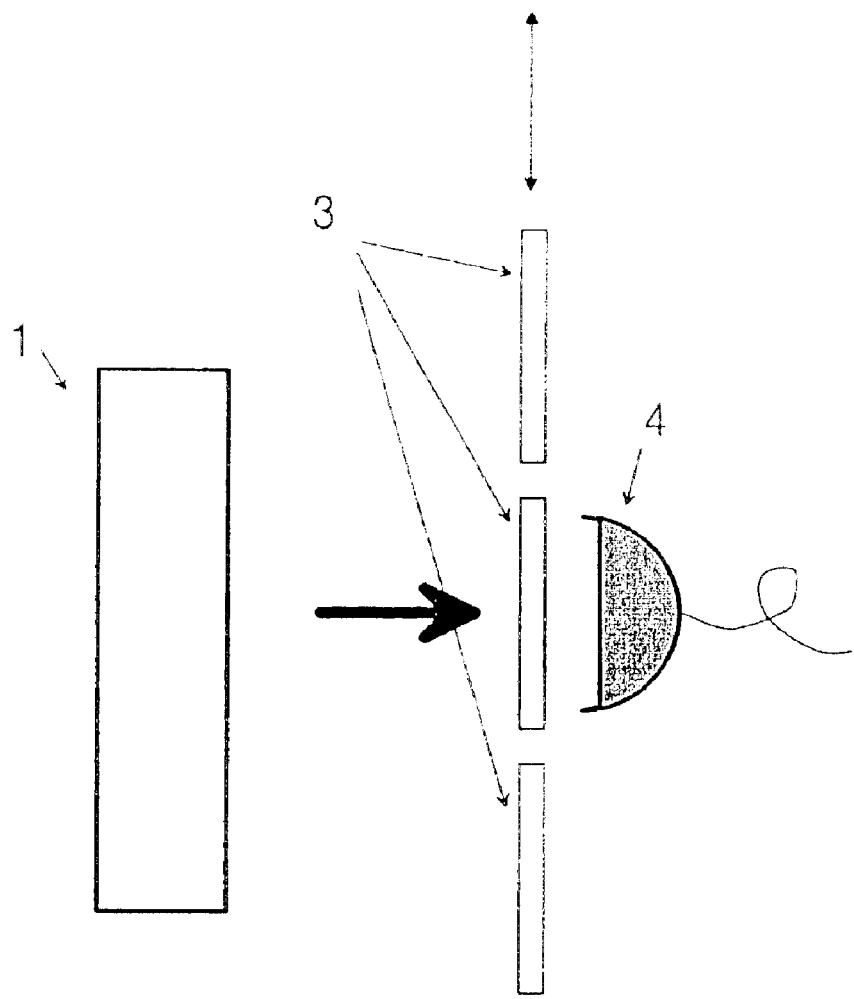
FIG. 4 is schematic of time-sequence detection of the present invention.

According to another aspect of the inventive concept detection may also be effected in a time-sequential manner as shown in FIG. 4. The transmitted or reflected radiation leaving the substance mixture 1 is detected by detector 4 upstream of which are arranged, in a time-sequential manner, the broad-band filters 3 calculated by means of the aforementioned algorithm.

Figure 5:
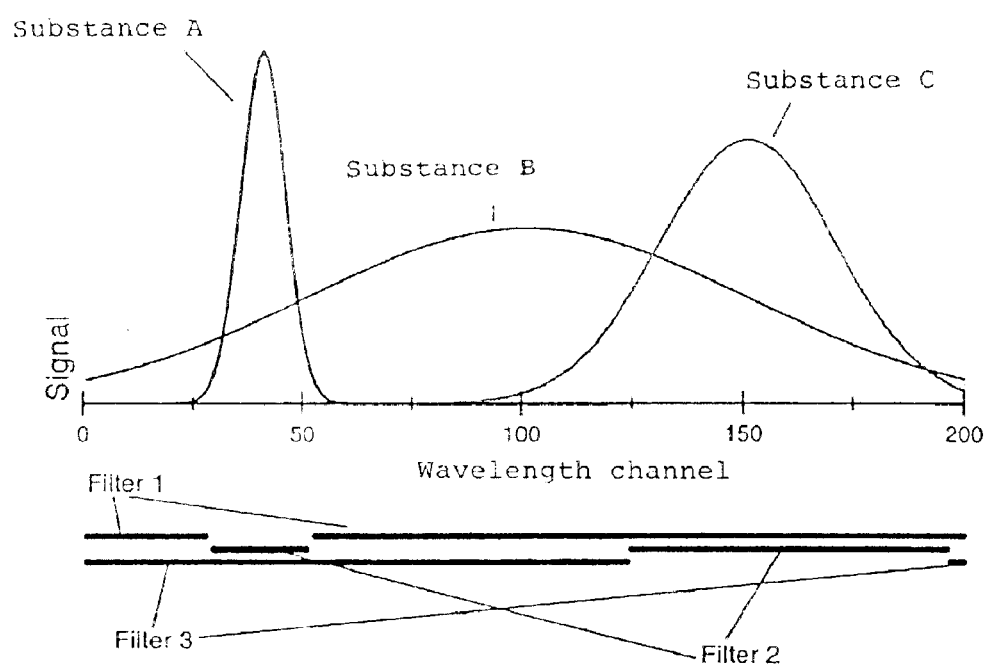
FIG. 5 is a depiction of the optimum filters of the present invention for a three-component system.

FIG. 5 shows, for illustration purposes, the optimum filters determined according to the invention of a three-component system. In the upper part the spectral properties of the three components are plotted. The three curves correspond to the three columns of system matrix E. In the lower part the transmitting spectral subranges of the optimum filters are represented by horizontal lines. It can be seen that each of the three filters essentially detects the signal of two of the three substances. The aforementioned algorithm for determining the filtering functions ensures that changes in the concentration of one or a plurality of substances cause maximum changes of the detector signals. By means of a matrix equation corresponding to (21) the concentration of the substances can be determined from the signal vector.

The algorithm according to the invention for determination of the filter matrix R is shown in FIG. 6. Each line of this matrix describes one of the binary transmission filters.

Figure 7:
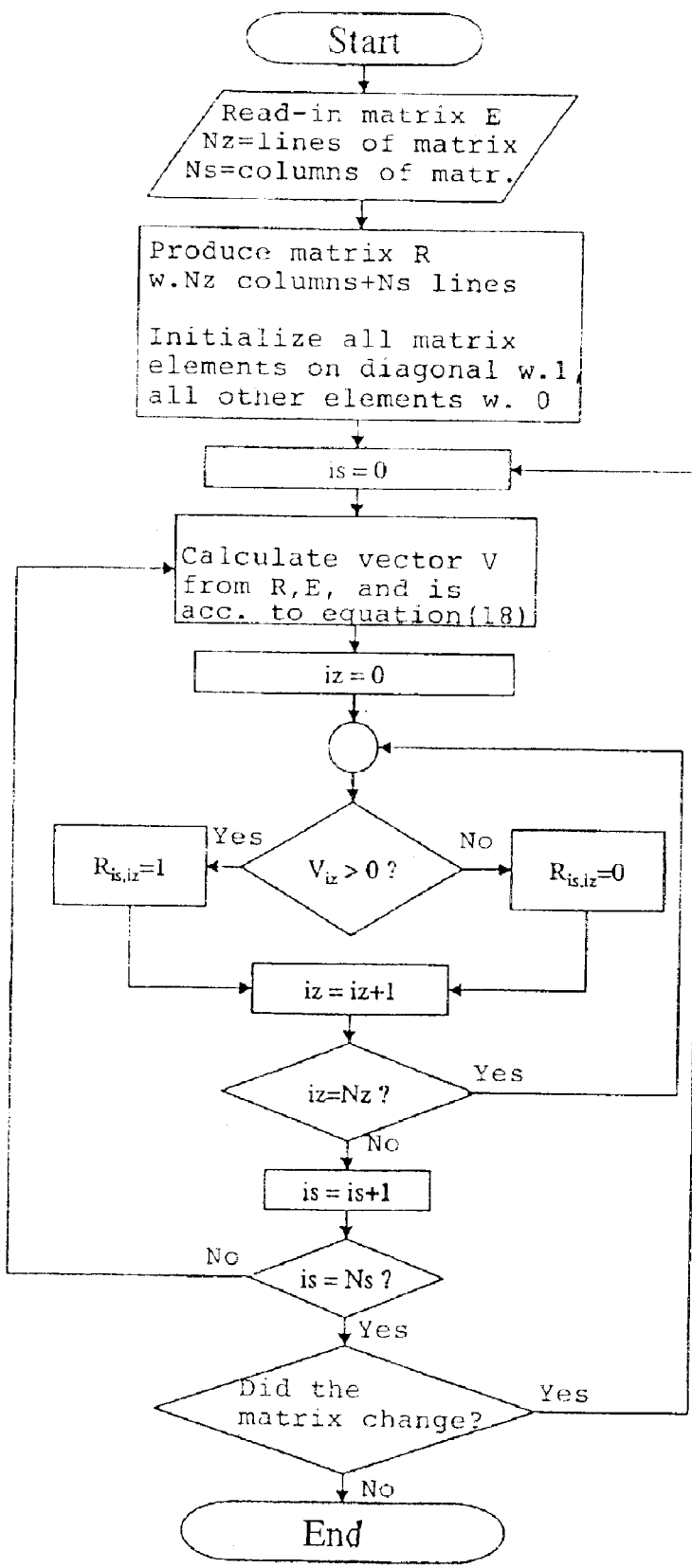
FIG. 7 is a flow chart of the method of the present invention.

FIG. 7 shows the algorithm as flow chart.

In another arrangement according to the invention, as shown in FIG. 8, the radiation is fed to the place of examination 2 with the aid of one or a plurality of glass fibres 6 and the scattered radiation is supplied from the place of examination to the detectors by means of a plurality of glass fibres 7. This arrangement does not include any beam splitter.

Figure 9:
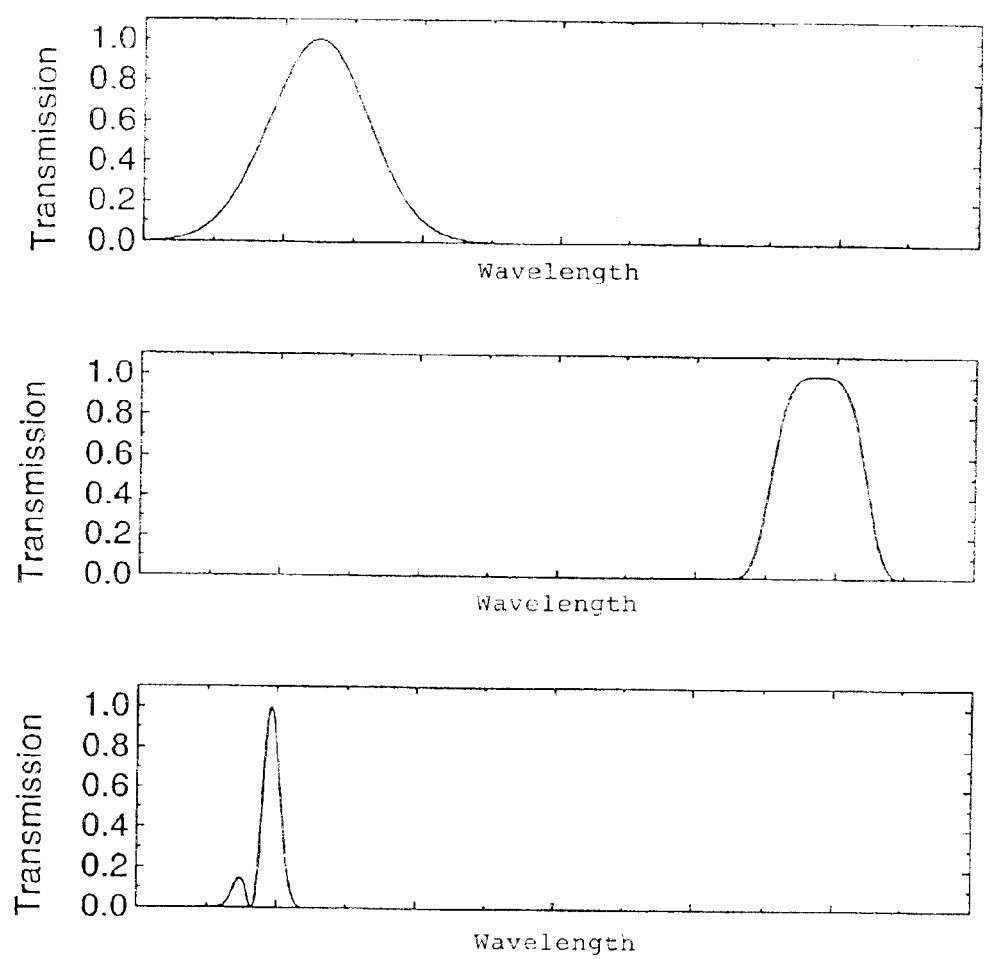
FIG. 9 is a depiction of broad-band, non-binary filtering functions of the prior art.

FIG. 9 shows, by way of example, broad-band non-binary filtering functions as currently used in the field of broad-band spectroscopy. By filter transmissions smaller than 1 in relevant spectral ranges the photon yield is reduced. By filter transmissions larger than 0 in irrelevant spectral ranges the signal-to-noise ratio is reduced. Both phenomena result in a suboptimum detection accuracy with regard to small substance concentrations.

Figure 10:
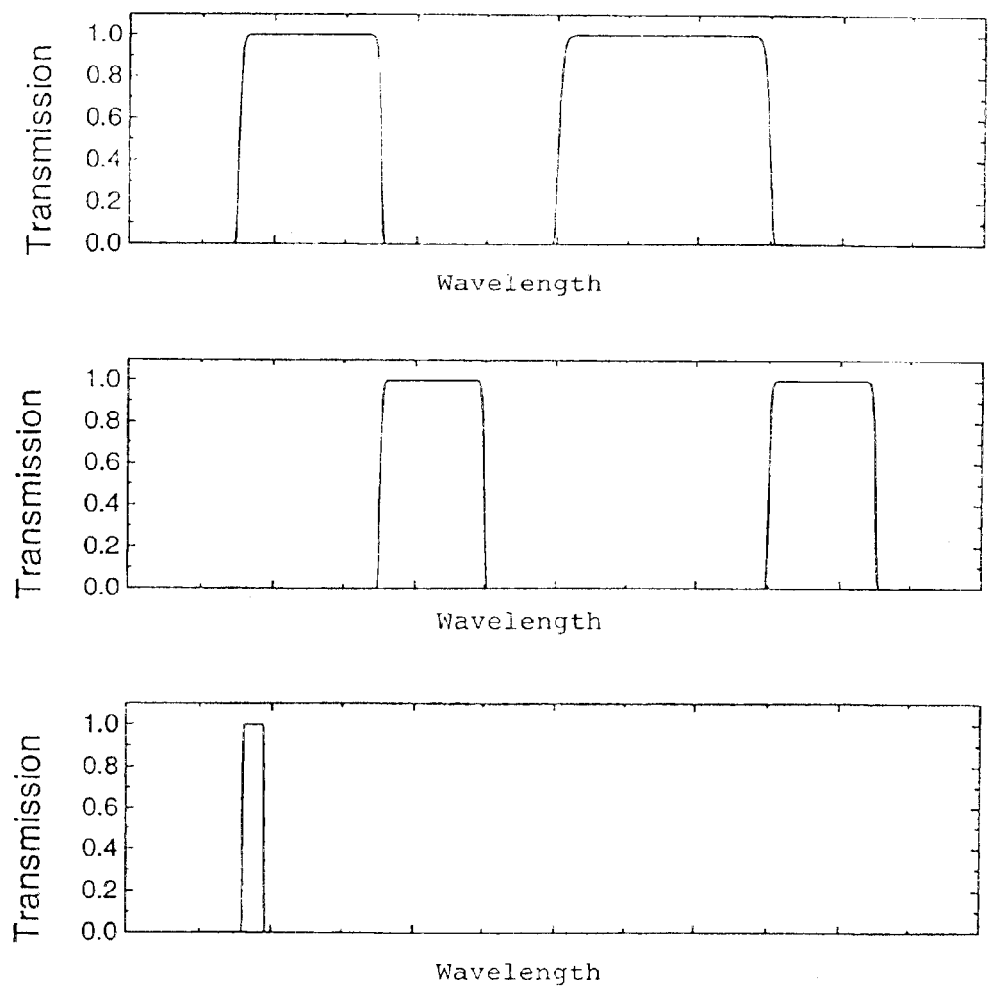
FIG. 10 is a depiction of broad-band filtering function of the present invention.

FIG. 10 shows, by way of example, a broad-band filtering function according to the invention which is distinguished in that each filter has a transmission of approximately One in one or a plurality of spectral subranges whereas in all other spectral subranges the transmission is approximately Zero.

FIG. 11 shows the typical absorption maxima and minima of glucose relative to water. For detection of blood glucose the pass-bands of at least one filter are selected in the range of the absorption maxima and the pass-bands of at least one further filter in the range of the absorption minima whereby the changes in the glucose concentration cause maximum changes in the detector signals thus resulting in maximum detection accuracy.

FIG. 12 shows the temperature dependence of the transmission of water in the wavelength range from 1.2 $\mu$m to 2.5 $\mu$m. It is known that the absorption of water shows a temperature-dependent spectrum shift. Said spectrum shift results in unwanted changes in the detector signals. In the wavelength range of approximately 1.38 $\mu$m the temperature-dependent shift is minimal. For determination of substance concentrations in an aqueous environment the pass-band of at least one detector is selected in this wavelength range such that the signal of this detector is available as temperature-independent reference signal.

FIG. 13 shows the seven binary filtering patterns for the transcutaneous determination of blood glucose concentrations. The spectral transmission of each filter is respresented by one horizontal line each. In the spectral subranges overlined by said line the respective filter has a transmission of essentially One whereas in all other spectral subranges it has a transmission of essentially Zero. The filtering patterns shown maximize the changes in the detector signals caused by the changes in the blood glucose concentrations.

List of Symbols $\lambda$—Wavelength
P—Spectral light efficiency
$\vec{P}$—Light efficiency vector. Vector whose components are made up of the values of the spectral light efficiency at various wavelengths
$\vec{\nabla}_{\vec{c}}\vec{P}$—Matrix whose element in the $i^{th}$ line and $j^{th}$ column is the partial derivation of the spectral light efficiency at the $i^{th}$ wavelength according to the concentration of the $j^{th}$ substance
$C_i$—Concentration of the $i^{th}$ substance
$\vec{C}$—Concentration vector. Vector whose components are made up of the values of the concentrations of the variable substances involved
$\vec{C}_0$—Reference concentration vector
$\Box C_i$—Change of the concentration of the $i^{th}$ substance as compared with the reference value
T—Ambient parameter (e. g. temperature or similar)
$\vec{C}'$—Generalized concentration vector. Vector whose components are made up of the values of the concentrations of the variable substances and the variable ambient parameters involved
L—Number of the wavelengths considered
N—Number of the variable quantities of the system (substances, ambient parameters)
D—Number of detectors
K—Number of the mixtures for calibration
E—System matrix reflecting the functional correlation between the change of the light efficiency vector and the change of the concentrations in the linear approximation
E'—Extended system matrix reflecting the functional correlation between the change of the light efficiency vector and the change of the generalized concentration vector in the linear approximation
R—Spectral response of a detector
$\vec{R}$—Response vector. The components are made up of the response of a detector at various wavelengths
R—Response matrix. The element in the $i^{th}$ line and $j^{th}$ column is the response of the $i^{th}$ detector at the $j^{th}$ wavelength
$S_i$—Signal of the $i^{th}$ detector
$\vec{S}$—Signal vector. The elements are made up of the signals of the various detectors
$\delta\vec{S}$—Change of the signal vector caused by deviation of individual or a plurality of generalized concentrations from the reference values
M—Matrix describing the functional correlation between the changes of the signal vector and the change of the generalized concentrations in the linear approximation
D—Number of detectors
B—Calibration matrix. The element in the $i^{th}$ line and $j^{th}$ column indicates the light efficiency measured in the $j^{th}$ substance mixture at the $i^{th}$ wavelength
$\tilde{B}$—Centered calibration matrix
H—Covariance matrix
X—Matrix whose column vectors are the M eigenvectors of the covariance matrix H with the maximum eigenvalues

What is claimed is:

1. Method for photometric determination of concentration changes in substance mixtures, comprising:

providing a spectral power from substance mixtures;

processing the spectral power at a plurality of binary spectral filters having a transmission that essentially only assumes the values One and Zero;

sending the transmissions in a time-sequential manner to a plurality of detectors; and determining concentration changes from signals from the plurality of detectors, wherein the transmitting spectral subranges of the filters are selected such that changes in the detector signals caused by changes in the substance concentrations and ambient parameters are maximized.

2. Method according to claim 1, further including the step of selecting the number of binary spectral filters used wherein the number selected corresponds at least to the number of relevant variable parameters.

3. Method according to claim 1, wherein the binary spectral filters are determined from spectrum-resolving calibration measurements in the case of unknown system matrix.

4. Method according to claim 1, wherein the binary filters are configured as reflection filters.

5. Method according to claim 1, further including the step of illuminating the substance mixture by a thermal light emitter.

6. Method for determination of substance concentrations in an aqueous environment, comprising:

providing a spectral power from the aqueous environment;

processing the spectral power at a plurality of binary spectral filters having a transmission that essentially only assumes the values One and Zero; provide that at least one of the filters acts as an internal reference filter at 1.38 $\mu$m sending the transmissions of spectral subranges to a plurality of detectors; and determining concentration changes from signals from the plurality of detectors, wherein the aqueous environment for determination includes blood glucose concentrations, wherein the plurality of binary spectral filters is from five to eight, and further wherein from three to four transmitting spectral subranges are used.

7. Method according to claim 6, wherein the spectral power from the aqueous environment is provided in a time-sequential manner.

8. Method according to claim 6, wherein the plurality of the bandpass filters lie in the spectral range between 0.6 and 2.5 μm.

9. Method according to claim 6, wherein for determination of blood glucose concentrations seven detectors are used.

10. Method according to claim 6, further including the step of providing radiation of a light source to the aqueous environment by means of one or a plurality of glass fibres.

11. Method according to claim 6, wherein the step of providing spectral power from the aqueous environment includes the use a glass fibre bundle.

12. Method for photometric determination of concentration changes in substance mixtures, comprising:

provifing a spectral power from substance mixtures;

processing the spectral power at a plurality of binary spectral filters having spectral transmissions that essentially only assumes the values One and Zero;

sending the transmissions to a plurality of detectors; and determining concentration changes from signals from the plurality of detectors, wherein the transmitting spectral ranges of the spectral filters are selected such that changes in the substance concentrations cause maximum changes in the detector signals.

13. Method for photometric determination of concentration changes in substance mixtures, comprising:

providing a spectral power from substance mixtures;

processing the spectral power at a plurality of binary spectral filters having a transmission that essentially only assumes the values One and Zero;

sending the transmissions to a plurality of detectors; and determining concentration changes from signals from the plurality of detectors;

wherein the binary filters are selected such that at least one of the filters lies in a known absorption band of a target substance, at least one further filter lies outside but in the immediate vicinity of said absorption band, and at least one further filter lies at a larger spectral distance at a dynamic-invariant place of absorption.

14. Method for photometric determination of concentration changes in substance mixtures, comprising:

providing the substance mixtures at a place of examination;

providing reflected or transmitted radiation by means of a glass fibre bundle from the place of examination;

processing the reflected or transmitted radiation at a plurality of binary spectral filters having transmissions that essentially only assumes the values One and Zero;

sending the transmissions to a plurality of detectors; and determining concentration changes from signals from the plurality of detectors.

15. Method according to claim 14, further including the step of feeding radiation of a light source to the place of examination by means of one or a plurality of glass fibres.

* * * * *